2 Sheets—Sheet 1.

J. J JOHNSTON.

Assignor, by mesne assignments, to THE AMERICAN HYDROCARBON GAS CO.

Process for Evaporating Liquids.

No. 8,374. Reissued Aug. 13, 1878.

WITNESSES
P. L. Durand
T. E. O'Brien

INVENTOR
James J. Johnston
by Wm. Ellsworth
his ATTORNEYS

2 Sheets—Sheet 2.

J. J JOHNSTON.

Assignor, by mesne assignments, to THE AMERICAN HYDROCARBON GAS CO.

Process for Evaporating Liquids.

No. 8,374. Reissued Aug. 13, 1878.

WITNESSES

H. L. Durand

T. E. O'Brien

INVENTOR

James J. Johnston

R. Hill Fellowes

His ATTORNEYS

UNITED STATES PATENT OFFICE.

JAMES J. JOHNSTON, OF COLUMBIANA, OHIO, ASSIGNOR, BY MESNE ASSIGNMENTS, TO THE AMERICAN HYDROCARBON GAS COMPANY, OF PITTSBURG, PENNSYLVANIA.

IMPROVEMENT IN PROCESSES FOR EVAPORATING LIQUIDS.

Specification forming part of Letters Patent No. 50,935, dated November 14, 1865; antedated November 2, 1865; Reissue No. 5,570, dated September 9, 1873; Reissue No. 8,374, dated August 13, 1878; application filed January 25, 1878.

DIVISION B.

*To all whom it may concern:*

Be it known that I, JAMES J. JOHNSTON, of Columbiana, in the county of Columbiana and State of Ohio, have invented a new and Improved Process for Evaporating Liquids; and I do hereby declare the following to be a full and exact description of the same, reference being had to the accompanying drawings, forming part of this specification.

The nature of this part of my invention consists in the process of obtaining a useful product by the union of air and steam with the vapors of hydrocarbon liquids in a highly-heated condition, which product may be passed through a condenser or otherwise used, according to the purpose for which it is to be employed.

The apparatus which I have employed for carrying this part of my invention into practice constitutes the subject of another division of this reissue, and is not herein claimed, but will be here described in order that the process and one mode of carrying it into practice may be fully and clearly understood.

Figure 1:
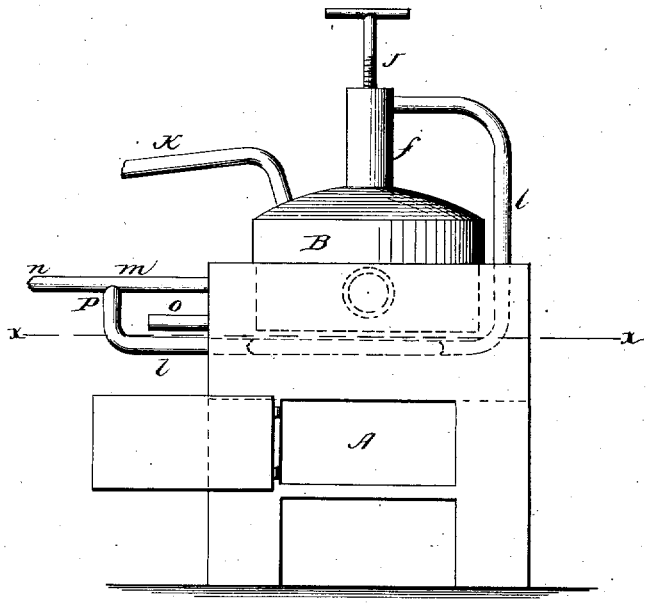
Figure 2:
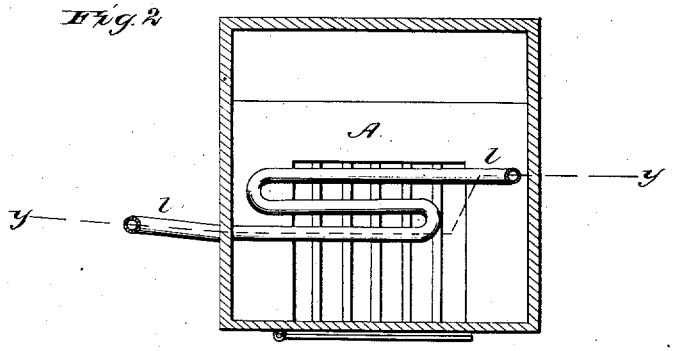
Figure 3:
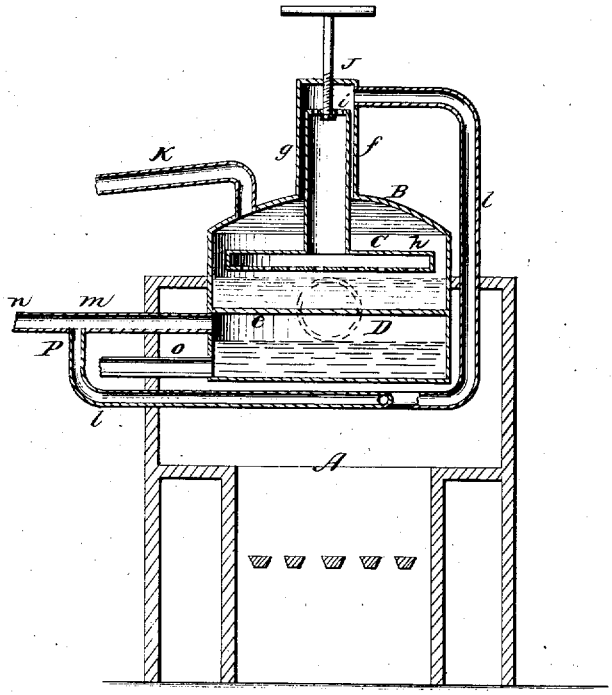

In the accompanying drawings, which form part of my specification, Figure 1 is a front elevation of the said apparatus. Fig. 2 is a horizontal section of the same at line *x* of Fig. 1. Fig. 3 is a vertical section of the same at line *y* of Fig. 2.

Similar letters of reference indicate the same parts.

In said drawings, A represents the furnace, and B represents the still or retort, which is divided into two compartments, C and D, by means of a partition, *e*. The compartment C is furnished with a hollow column, *f*, into the bore of which is fitted another column, *g*, on the lower end of which is a hollow disk, *h*, the lower face of which is perforated with a large number of small openings, and in the upper end of the column *g* are a number of openings, *i*.

The column *g* and its disk *h* are suspended in the column *f* and still C by means of a screw, J, whereby they can be raised or lowered in the still, so that the disk may be just above the liquid therein or lowered below its surface to any desired point. To the crown of the still or retort is a pipe, *k*, for the purpose of carrying off the vapor evolved from the liquid in the still. To the upper end of the column *f* is attached a pipe, *l*, which passes down into the furnace A and, traversing back and forth under the still, passes out of the furnace, and is connected to the pipe *m* communicating with the upper portion of the compartment D of the still or retort. Near the bottom of the compartment D is a pipe, *o*, communicating with the water-supply. To the branch *n* of the pipe *m* should be attached an air-blast device.

From the foregoing description the skillful mechanic will readily understand the construction and arrangement of the mechanical devices herein shown and described; but I wish it clearly understood that I do not confine myself to any particular construction of device, so far as my process is concerned, as the construction of the various parts may be varied without departing from the principle of the invention.

The compartment A being supplied with water, and the compartment C with the oil or other liquid to be evaporated and vaporized, fire is made in the furnace, which will generate steam in the compartment D, which will heat the liquid in the compartment C, and as soon as a sufficient pressure of steam is generated it will pass through the pipe *m*, and, the air-blast device being put in operation, the steam and air will combine at the point P, and entering the pipe *l* will pass through it and enter the column *f*, and pass through the openings *i* into the column *g*, thence down into the disk *h*, and out through the small openings therein, and, acting on the surface of the heated liquid, will rapidly evaporate and vaporize it, and the air and steam combined and superheated, having performed its office on or in the liquid in the compartment C, and having commingled with the vapor of the liquid, the mixture or compound resulting from the union of hydrocarbon, steam, and air when at a high temperature will pass off through the pipe *k* to a condenser or elsewhere, according to the purpose for which it is to be employed.

Having thus described my invention, what I claim herein is—

The herein-described process of obtaining a useful product from air, steam, and the vapor of hydrocarbon liquids—namely, by uniting them in a highly-heated condition.

JAMES J. JOHNSTON.

Witnesses:
WM. BLACKSTOCK,
MELVILLE CHURCH.